United States Patent [19]

Epstein

[11] Patent Number: 4,757,089
[45] Date of Patent: Jul. 12, 1988

[54] INCREASING AQUEOUS HUMOR OUTFLOW

[75] Inventor: David L. Epstein, Wayland, Mass.

[73] Assignee: Massachusetts Eye and Ear Infirmary, Boston, Mass.

[21] Appl. No.: 948,443

[22] Filed: Dec. 30, 1986

Related U.S. Application Data

[63] Continuation of Ser. No. 745,325, Jun. 14, 1985, abandoned.

[51] Int. Cl.$^4$ ............................................. A61K 31/19
[52] U.S. Cl. .................................. 514/571; 514/913
[58] Field of Search .............................. 514/571, 913

[56] References Cited

U.S. PATENT DOCUMENTS 3,255,241 6/1966 Schultz.

FOREIGN PATENT DOCUMENTS 883792 10/1971 Canada ................................ 514/571
1141422 1/1969 United Kingdom ................ 514/571

OTHER PUBLICATIONS

Chem. Abst. 84:99192h, (1976)-Guenther et al.
Invest. Ophthalmol. Vis. Sci. 22 (6)–752–756, (1982)–Epstein et al.
Magro et al., (1983), Int. Archs. Allergy Appl. Immun. 72, 41.
Epstein et al., (1970), Invest. Ophthalmol. 9 (8), 629.
Lindenmayer et al., (1982), Invest. Ophthalmol. Vis. Sci. 24 (6), 710.
Epstein et al., (1981), Invest. Ophthalmol. Vis. Sci. 20 (5), 625.
Anderson et al., (1980), Invest. Ophthalmol. Vis. Sci. 91 (1), 13.
Kahn et al., (1983), Invest. Ophthalmol. Vis. Sci. 24 (3), 1283.
Scott et al., (1984), Invest. Ophthalmol. Vis. Sci. 25 (5), 599.
Freddo et al., (1984), Invest. Ophthal. Mol. Sci. 25 (3), 278.

Primary Examiner—Douglas W. Robinson

[57] ABSTRACT

A method of increasing aqueous humor outflow in the eye of a human patient including topically administering to the eye an outflow increasing amount of a compound characterized in that it contains one or more groups capable of reacting with sulfhydryl groups in the trabecular meshwork of the eye, and it has a margin of safety of at least 2.0.

3 Claims, No Drawings

INCREASING AQUEOUS HUMOR OUTFLOW

This application is a continuation of Epstein U.S. Ser. No. 745,325, filed on June 14, 1985 now abandoned.

BACKGROUND OF THE INVENTION

This invention relates to the treatment of disorders of the human eye, particularly glaucoma.

Glaucoma is characterized by intraocular pressure resulting at least in part from a diminished outflow of aqueous humor through the trabecular meshwork.

Epstein et al. (1982) Invest. Ophthalmol. Vis. Sci. 22, 6, 752-756 describes experiments in which eyes from dead calves, macaques, and baboons were fitted with stainless-steel corneal fittings. The eyes were perfused, by filling the anterior chambers at 15 mm Hg and 22° C., with a solution containing the toxic compound N-ethylmaleimide (NEM), a compound reactive with sulfhydryl groups. It was found that a "dosage of NEM of 4.7 in mM or greater produced a significant increase in the facility of outflow in the calf eye." "NEM also caused an increase in outflow in the monkey eye." The paper goes on:

Our results indicate that chemical modification of cellular —SH groups can also alter the egress of aqueous humor from the trabecular meshwork. Cellular or intercellular permeability to fluid flow in the aqueous outflow channels may be influenced by the state of cell membrane protein sulfhydryls. Trabecular —SH groups may be intimately involved in the normal process of aqueous outflow, especially if located at sites of normal resistance in the juxtacanalicular tissue or endothelium of Schlemm's canal. Alternatively, —SH groups may exert only a secondary influence on outflow through nonspecific structural changes in trabecular cell membranes.

SUMMARY OF THE INVENTION

In general, the invention features a method of increasing aqueous humor outflow in the eye of a human patient comprising topically administering to the eye an outflow increasing amount of a compound characterized in that it contains one or more groups capable of reacting with sulfhydryl groups in the trabecular meshwork of the eye, it has an octanol: water partition coefficient of at least 0.005, and it has a margin of safety of at least 2.0. The high lipophilicity (expressed in terms octanol: water partition coefficient) enables the compounds to penetrate the membrane of the cornea of the eye, so that they can be applied topically. Safe topical administration is also facilitated by low toxicity (expressed in terms of margin of safety).

Another aspect of the invention features increasing aqueous humor outflow in a patient's eye by the microinjection of an effective, low-toxicity, sulfhydryl-reacting group directly into the trabecular meshwork.

In both methods of administration, preferred compounds are ethacrynic acid or analogs thereof, and pharmaceutically acceptable salts thereof.

The invention provides effective, non-surgical treatment of glaucoma in a manner which increases fluid outflow while causing minimal non-fluid related ocular functions.

Other features and advantages of the invention will be apparent from the following description of the preferred embodiments thereof, and from the claims.

DESCRIPTION OF THE PREFERRED EMBODIMENTS

As mentioned above, the compounds useful in the methods of the invention have a number of required properties, now discussed in greater detail.

Sulfhydryl Reactivity

The compounds must contain chemical groups which are capable of reacting with the sulfhydryl groups of the trabecular meshwork to increase aqueous humor outflow. The compounds must react with the sulfhydryl groups in a manner which does not cause an unacceptable amount of swelling of the cells of the trabecular meshwork, particularly the inner wall endothelial cells of Schlemm's canal, because swelling can decrease outflow. "Unacceptable amount of swelling", as used herein, means an amount of swelling which completely counteracts the outflow increasing effects of the compounds, resulting in no net outflow increase. Whether swelling is caused by a particular compound can be determined by testing the compound in the system described in Epstein et al., id, and examining the trabecular meshwork cells morphologically.

Suitable sulfhydryl reactive groups include $C=C$, $C=O$, sulfhydryl, alkyl (e.g., methyl or ethyl) and aryl (e.g., phenyl) substituted with a good leaving group, e.g., halogen, tosyl, or mesyl. Preferably, in the case of substituted alkyl groups, substitution is primary, rather than secondary or tertiary, for greater reactivity.

Toxicity and Margin of Safety

As used herein, "margin of safety" refers to the ratio of the dosage of the outflow increasing compounds which causes medically unacceptable toxic side effects, and the dosage which causes substantial (i.e., medically useful) increase in aqueous humor outflow in a typical human patient with advanced open angle glaucoma. The margin of safety of the compounds must be at least 2.0, and more preferably at least 4.0.

It is also important that the compounds not produce, at effective dosages, long-term deleterious changes in the eye.

Lipophilicity

Compounds to be administered to the eye topically must be sufficiently lipophilic to penetrate the corneal membrane. Sufficient lipophilicity can be provided by a non-polar structure, the presence of at least one aryl group (e.g., a substituted or unsubstituted phenyl ring), at least one halogen atom, and/or hydrophobic alkyl groups. For lipophilicity, it is also desirable that the compound not carry excessive charge; i.e., of absolute value greater than 2, at physiological pH.

Lipophilicity is expressed in terms of octanol: water coefficient, determined by the standard technique of radiolabelling the compound and introducing a small amount into equel volumes of octanol and Tris buffer (50 mM, pH 7.4). The coefficient of the compounds is preferably at least 0.005, and more preferably at least 0.01.

Administration

The outflow-increasing compounds can be administered either topically or by microinjection into the trabecular meshwork. For topical administration, the compound is dissolved in a pharmaceutically acceptable carrier substance, e.g., physiological saline. For compounds having limited water solubility (e.g., the sodium salt of ethacrynic acid, soluble only to about 0.04 g in water) the liquid carrier medium can contain an organic solvent, e.g., 3% methyl cellulose. Methyl cellulose provides, by its high viscosity, increased contact time between the compound and the eye surface, and therefore increased corneal penetration. Corneal penetration can also be increased by administering the compound mixed with an agent which slightly disrupts the corneal membrane, e.g., 0.025% benzalkonium chloride. Administration is by periodically (e.g., one time per week to ten times per day) applying drops of the compound in solution using an eye dropper, such that an effective amount of the compound is delivered through the cornea to the trabecular meshwork. The amount of the compound to be delivered in one administration will depend on individual patient characteristics, e.g., severity of disease, as well as characteristics of the compound, e.g., the specific affinity for trabecular meshwork sulfhydryl groups, and the magnitude of the margin of safety. Typically, each drop contains 50–100 microliters of a 5–10 mM solution of the compound, so that 0.025 to 0.10 moles of the compound are delivered to each eye per day.

Direct microinjection of the solubilized compound into the trabecular meshwork offers the advantage of concentrating the compound in the location where it is needed, while avoiding the possibility of side effects resulting from generalized exposure of the eye to the compound. microinjection also provides the advantage of permitting infrequent periodic administration, e.g., every few weeks, months, or even years, in contrast to the more frequent administrations required in the case of topical administration. Also, direct microinjection may promote the washing out of the trabecular meshwork of extracellular material interferring with fluid outflow. Dosage for microinjection, like that for topical administration, varies with the above-mentioned parameters. Typically, microinjection dosage is such that a final concentration of the compound within the trabecular meshwork of 0.01 to 1.0 mM is reached.

In Vivo Use of Ethacrynic Acid

Ethacrynic acid (sodium salt) was used to increase aqueous humor outflow in cynomologous monkeys, as described below. Ethacrynic acid can be purchased from Merck, Sharp, and Dome, and is described in U.S. Pat. No. 3,255,241, hereby incorporated by reference. Ethacrynic acid has the chemical formula [2,3-dichloro-4-(2-methylene-1-oxobutyl) phenoxy] acetic acid. Any suitable analogs described in U.S. Pat. No. 3,255,241 can also be used as described herein.

Each animal was randomly assigned one eye for the experimental and the other for its control perfusion. The animals were fasted the night before the experiment. They were anesthetized intramusclarly with Methohexital Sodium 15 mg/kg and Pentobarbital Sodium 35 mg/kg. Supplemental anesthesia as required was carried out with Pentobarbital 10 mg/kg/hour. Needles were placed through the cornea into the anterior chamber and a two-step constant pressure perfusion method was performed in order to determine aqueous humor outflow facility. The basic medium for perfusion was Dulbecco's phosphate buffered saline with added 5.5 mM glucose. A 10 microliter bolus of the experimental or control solution (that would produce the desired final concentration in the anterior chamber) was injected through a T shaped connector piece in the infusion line.

Each vial of ethacrynic acid contained ethacrynate sodium powder equivalent to 50 mg of ethacrynic acid. The inactive ingredients were 62.5 mg mannitol and 0.1 milliliters thimerosol (as preservative). The powder was diluted with the above basic medium (Dulbecco's with added glucose) to yield the desired concentration. The solution was mixed at room temperature until dissolved, and the pH was determined (always 7.2) before use; the solution was filtered with a 0.2 micron filter (Nuclepore); this produced a solution which was stable for twenty four hours.

The control solution was composed of 9.5 mg sodium chloride (to osmoticly balance the equal experimental solution), 62.5 mg mannitol and 0.1 milliliter thimerosol dissolved in Dulbecco's phosphate buffered saline with 5.5 mM added glucose to yield the desired concentration.

During perfusion experiments, a 10 microliter bolus injection was made using a Hamilton syringe. Since the monkey anterior chamber is approximately 200 microliters, our calculations were as follows. To achieve a final concentration of 0.5 mM ethacrynic acid, 10 microliters of 10 mM ethacrynic acid was infused.

Experiments were carried out using final ethacrynic acid concentrations in the aqueous humor of 0.1 mM to 0.5 mM. There were at least three animals and separate experiments carried out for each of the concentrations 0.1 mg, 0.25 mM, and 0.5 mg.

At 0.5 mM, a mean increase in fluid outflow facility of 140% due to ethacrynic acid was determined, compared to no change in the control perfused eye. At 0.25 mM, approximately half the animals perfused responded with a substantial increase in outflow facility due to ethacrynic acid and the other half did not. At lower dosages there was no effect. One animal was perfused at 1.0 mM and demonstrated a 355% increase in the experimental eye compared to an 18% increase in the control eye.

There were no apparent corneal or crystalline lens changes. Specifically, there was no chronic corneal edema or opacities or cataract formation. At dosages above 0.25 mM some of the animals developed a dilated pupil in the ethacrynic treated eye. A small number of animals in both the experimental and control eyes developed adhesions of the iris to the peripheral cornea which was believed to result from the perfusion technique itself rather than the drug administration.

Intraocular pressure could not be reliably taken until a few days after the perfusion experiments (due to the possibility of leaks in the cornea through the needle placements), and at that time intraocular pressure was symmetrical and normal in both eyes.

For rabbit experiments Dutch-belted rabbits of either sex weighing 1.5 to 2 kg were used for topical studies. Each animal was randomly assigned one eye for the experimental and the other for its control solution. Intraocular pressure was measured using a Digilab Pneumotonometer. Any animals showing asymmetry of intraocular pressure greater than 2 mm were excluded form the study.

The protocol was as follows. Baseline intraocular pressure was taken in each eye using 0.5% proparacaine hydrochloride for topical anesthesia. Then a 100 microliter drop of either control solution or ethacrynic acid dissolved in 3% methylcellulose was instilled into one of the two eyes. In a half hour this was repeated. Two hours later intraocular pressure was measured in each eye. In some animals intraocular pressure was also measured five hours later and all animals had measurement of intraocular pressure the following day.

Ethcrynic acid powder was dissolved in 3% methylcellulose to yield the desired concentration. The solution was mixed at room temperature for one hour and was stable for twenty four hours. A similar osmotically balanced control solution was prepared. 3% methylcellulose was prepared as follows: methylcellulose powder (4000 CPS) was obtained from Dow company (lot number 14728). A 3% solution was prepared from powder dissolved in distilled water using low heat for several hours. The solution was refrigerated over night to yield a transparent, viscous fluid. The pH of the solution was determined by mixing one part of the control or experimental solution with five parts of distilled water. The pH ranged between 6.2 and 6.5 for both the control and experimental solutions. The 3% methylcellulose solution was refrigerated when not in use.

The pressure data was as follows: for 5 mM ethacrynic acid in 3% methylcellulose in eight animals, two hours following instillation intraocular pressure in the ethacrynic treated eye had decreased from 22.4 to 19.6 mmHg (p less than 0.01) whereas the control eye had shown a slight increase from 21.5 to 23.1 mmHg. The next day intraocular pressure was equal in the two eyes being 22.4 in the ethacrynic treated eye and 22.7 in the control eye.

In fourteen rabbits treated with 10 mM ethacrynic acid and 3% methylcellulose twenty four hours after instillation intraocular pressure in the ethacrynic eye had changed from 23.0 to 20.0 mmHg whereas in the control eye from 22.9 to 24.2 mmHg. p was less than 0.001.

For studies at 5 mM concentration, there was slight conjunctival injection following administration. There were no other side effects noted. Following administration of 10 mM ethacrynic acid moderate conjunctival injection and signs of irritation were apparent.

At higher concentrations signs of corneal toxicity (corneal edema) and anterior chamber inflammation were apparent for several days. However, these resolved without apparent seguelae.

Other embodiments are within the following claims.

I claim:

1. A method of increasing aqueous humor outflow in the eye of a human patient to treat glaucoma in said patient, said method comprising topically administering to said eye an outflow increasing amount of ethacrynic acid, or an analog of ethacrynic acid which contains a chemical group capable of reacting with sulfhydryl groups in the trabecular meshwork of said eye, has a margin of safety of at least 2.0 and has an octanol: water partition coefficient of at least 0.005.

2. The method of claim 1 wherein said outflow increasing compound is ethacrynic acid or a pharmaceutically acceptable salt thereof.

3. A method of increasing aqueous humor outflow in the eye of a human patient to treat glaucoma in said patient, said method comprising administering by microinjection to the trabecular meshwork of said eye an outflow increasing amount of ethacrynic acid, or an analog of ethacrynic acid which contains a chemical group capable of reacting with sulfhydryl groups in said trabecular meshwork, and has a margin of safety of at least 2.0.

* * * * *